United States Patent [19]
Silverberg

[11] Patent Number: 5,823,984
[45] Date of Patent: Oct. 20, 1998

[54] EXPANDABLE WRAP WITH MULTIPLE PANELS AND ATTACHABLE POCKET

[76] Inventor: Ian Silverberg, 170 Los Carneros Way, Goleta, Calif. 93117

[21] Appl. No.: 661,199

[22] Filed: Jun. 10, 1996

[51] Int. Cl.⁶ .................................................. A61F 5/00
[52] U.S. Cl. ............................ 602/61; 128/876; 128/882; 602/19; 602/62; 602/63; 607/108; 607/112
[58] Field of Search ...................................... 602/2, 41–47, 602/60, 61, 62, 63, 64, 65, 66, 74, 75, 76, 77, 78, 79, 67; 128/845, 846, 856, 869, 873, 877, 878, 879, 880, 881, 882, 887, 888, 889; 2/455, 16, 22, 170

[56] References Cited

U.S. PATENT DOCUMENTS

| | | |
|---|---|---|
| 2,606,005 | 8/1952 | Poux . |
| 4,081,150 | 3/1978 | Tyson . |
| 4,303,239 | 12/1981 | Walsh, Jr. . |
| 4,461,030 | 7/1984 | Knudsen . |
| 4,527,566 | 7/1985 | Abare . |
| 4,556,055 | 12/1985 | Bonner, Jr. . |
| 4,586,506 | 5/1986 | Nangle . |
| 5,016,629 | 5/1991 | Kanare . |
| 5,020,711 | 6/1991 | Kelley . |
| 5,146,625 | 9/1992 | Steele et al. . |

OTHER PUBLICATIONS

Advertisement from "Sky Mall Catalog", p. 129.

*Primary Examiner*—Richard J. Apley
*Assistant Examiner*—Kim M. Lee
*Attorney, Agent, or Firm*—Haverstock & Owens LLP

[57] ABSTRACT

An expandable wrap includes one or more panels with exterior and interior surfaces of a fabric loop-type material. Hook-type fasteners which mate with the fabric loop-type material are used to secure adjoining panels together to form a wrap of an appropriate size to snugly fit around a body area without the need for straps or elastic bands. Preferably, three hook-type fasteners are coupled to a right edge of each panel to provide securing means for securing the panel to an adjoining panel. One or more pockets, capable of holding hot or cold thermo packs, supports and weights, are removably attached to the interior surface of the panels forming a wrap. A surface of the pocket includes hook-type fasteners which will removably secure the pocket to the fabric loop-type material on the interior surface of the panels of the wrap.

15 Claims, 2 Drawing Sheets

EXPANDABLE WRAP WITH MULTIPLE PANELS AND ATTACHABLE POCKET

FIELD OF THE INVENTION

The present invention relates to the field of therapeutic devices and wraps. More particularly, the present invention relates to the field of therapeutic devices and wraps used to hold cold or hot packs in contact with an area of the body or to provide support or hold weights for exercise of a body part.

BACKGROUND OF THE INVENTION

Ice packs and hot water bottles have been used in the treatment of aches, pains, muscle soreness and other injuries for a long time. It has been learned that the treatment of such injuries can be enhanced by the application of cold or heat to the injured area, for prescribed periods of time. Thermo packs from sub-freezing cold to almost scalding are used to speed and enhance the healing process of many injuries and other ailments such as arthritis. Some treatment programs prescribe alternating heat and cold on an injured area to stimulate the restorative process within the injured area.

Pouches, holders or coverings for use with heating pads, hot water bottles and hot/cold packs are well known. The pouch or covering is normally used as a barrier between the thermo pack and the user's skin, serving several purposes. The pouch or covering may be used to hold moisture when used in conjunction with a hot pack for the purpose of administering moist heat. The pouch or covering may extend the pack's useful life by protecting the pack from sharp objects which may puncture or tear the pack. Another important use of the pouch is to protect the wearer's skin from injury or discomfort due to the extreme temperatures of hot and cold which the thermo pack may exhibit.

Bonner, Jr. teaches a cold compress or bandage in U.S. Pat. No. 4,556,055, issued on Dec. 3, 1985, and entitled COLD COMPRESS. Before applied to the injured area, the bandage taught by Bonner, Jr. is first soaked or dampened with water and cooled. The bandage is then secured by a hook and loop fastener to a panel and straps. The wearer then places the bandage over the injured area and secures it to the injured area using the panel and straps. A plurality of pockets are included on the bandage for providing support or additional cooling. The cold compress of Bonner, Jr. is not expandable, does not allow multiple configurations and includes the pockets on the bandage.

Kanare teaches a pack for holding hot or cold packets in U.S. Pat. No. 5,016,629, issued on May 21, 1991 and entitled HOT AND COLD BODY PACK. This pack taught by Kanare includes an integral bag for holding hot or cold packets. Kanare teaches that multiple packs, each having a bag, can be attached together to cover larger body parts. A strap is positioned through loops on the packs and is used to secure the bags on the wearer, over the injured area.

Kelley also teaches a pouch for holding hot or cold packets in U.S. Pat. No. 5,020,711, issued on Jun. 4, 1991 and entitled POUCH FOR REUSABLE HOT/COLD PACKS FOR MEDICAL USAGE. This pouch taught by Kelley also includes an integral pocket for holding hot or cold packets. One or more of these pouches can be connected together using hook and loop fasteners. The pouches are secured to the wearer, over the injured area, by elastic bands or extension elastic bands which are wrapped around the wearer's body and attached to the pouches.

What is needed is a wrap which includes one or more panels, connected together, and can be snugly fitted around and secured over the appropriate area of the wearer's body without requiring the use of straps or elastic bands. What is further needed is a multiple panel wrap to which a pocket for holding a hot or cold pack can be attached and removed, from any area of the wrap.

SUMMARY OF THE INVENTION

An expandable wrap includes one or more panels with exterior and interior surfaces of a fabric loop-type material. Hook-type fasteners which mate with the fabric loop-type material are used to secure adjoining panels together to form a wrap of an appropriate size to snugly fit around a body area without the need for straps or elastic bands. Preferably, three hook-type fasteners are coupled to a right edge of each panel to provide securing means for securing the panel to an adjoining panel. One or more pockets, capable of holding hot or cold thermo packs, supports and weights, are removably attached to the interior surface of the panels forming a wrap. A surface of the pocket includes hook-type fasteners which will removably secure the pocket to the fabric loop-type material on the interior surface of the panels of the wrap.

DETAILED DESCRIPTION OF THE PREFERRED EMBODIMENT

An expandable wrap of the present invention is made up of one or more panels of similar construction. The number of panels necessary to form the wrap depend on the size of the specific body part over which the wrap is to be applied. In this manner, panels can be added and removed from a wrap to form the appropriate size. Adjoining panels within the wrap are secured together by hook and loop fasteners. The outer surface of each panel is formed of a loop-type fabric capable of receiving and securing to a hook fastener. Preferably, three fasteners are coupled to a right edge of each panel to provide ready securing means for securing the panel to another panel. These fasteners are each hook fasteners which will attach to the loop-type outer surface of a panel. Because the fasteners can be attached anywhere over the surface of a panel, a wrap can be made to snugly and securely fit around a specific body part without the need for straps or elastic bands.

The inside surface of each panel is also formed of a loop-type fabric capable of receiving and securing to a hook-type fastener. A pocket, capable of holding hot or cold thermo packs, supports or weights, includes hook-type fasteners on one of its outer surfaces so that the pocket can be secured to the interior of a wrap for applying a thermo pack, weights or support to the body part. Because of the construction of the panels, the wrap provides an insulating and comfortable support for the pocket and enhances the treatment to the body part. In this manner, one or more pockets can be affixed anywhere to the interior of the wrap, as appropriate.

Figure 1:
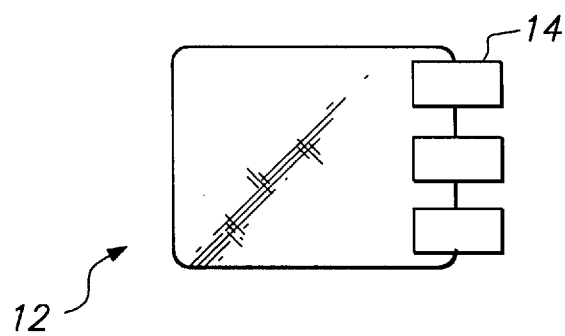
FIG. 1 illustrates a single panel according to the present invention.
Figure 4:
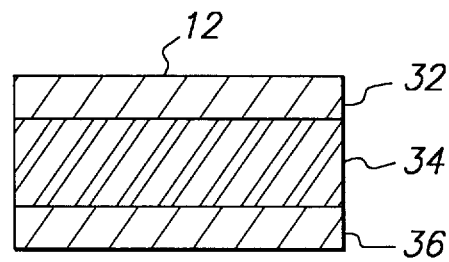
FIG. 4 illustrates a cross section of a panel of the present invention.

A panel according to the present invention is illustrated in FIG. 1. The panel 12 preferably includes three fasteners 14, stitched to its right edge. A cross-section showing the construction of a panel is illustrated in FIG. 4. Preferably, the panel 12 includes three layers, sealed together to form an integral construction. An outer layer 32 of the panel 12 is a loop-type fabric layer for receiving and securing to hook fasteners. An interior layer 36 of the panel 12 is also a loop-type fabric layer for receiving and securing to hook fasteners. In between the outer layer 32 and the interior layer 36 is a rubber insulating foam layer 34 to provide strength and shape to the panel 12. The rubber insulating foam layer 34 is sealed to both the outer layer 32 and the interior layer 36 to form an integral construction.

Each of the fasteners 14 includes a surface having hook-type fasteners which will securely fasten to the loop-type fabric on the outer surface of a panel. The fasteners 14 are preferably sewn to the panel 12 and extend over the edge of the panel for securing to an adjoining panel (not shown). Alternatively, the fasteners are not sewn to a panel but secured to two adjoining panels using only the hook-type fasteners. As will be apparent to those skilled in the art, the fasteners 14 could also be attached on other edges of the panel for forming wraps of various shapes, sizes and thicknesses.

Figure 3:
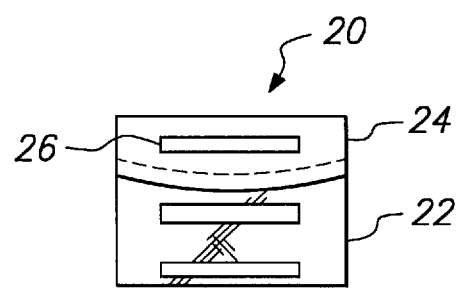
FIG. 3 illustrates a pocket of the present invention.

A pocket 20 for holding hot or cold thermo packs, supports or weights is illustrated in FIG. 3. The pocket 20 includes a lower flap 22 and an upper flap 24, with the upper flap extending over the lower flap 22, thereby forming a pouch through which packs can be inserted or removed. An outer surface of the pocket 20 illustrated in FIG. 3 is preferably constructed of a vinyl material and includes the hook-type fasteners 26 for securing the pocket 20 to the loop-type fabric layer interior surface of a wrap. The outer surface of the pocket 20 illustrated in FIG. 3 will therefore be adjacent to the interior surface of the wrap when the pocket is secured to the interior of the wrap. The opposite surface of the pocket 20 will therefore be in contact with the wearer's skin and is preferably constructed of a soft, absorbent fabric to provide a comfortable surface to the wearer. To insert a thermo pack, weight or support into the pocket 20, the pocket 20 is disconnected from the wrap and the thermo pack, weight or support is inserted into the pocket 20 by lifting the upper flap 24 away from the lower flap 22 and thereby exposing the interior of the pocket 20. The pocket 20 is then secured to the interior of the wrap by pressing the hook-type fasteners 26 against the interior surface of the panels which make up the wrap.

Figure 2:
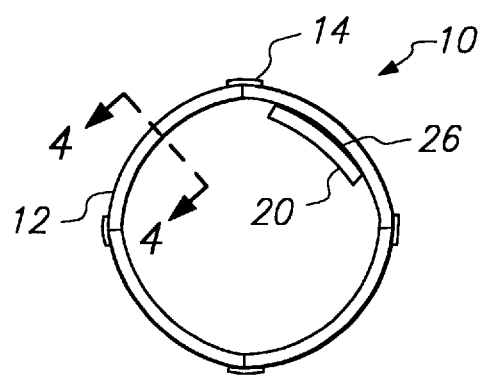
FIG. 2 illustrates a wrap including four panels and a pocket, according to the present invention.

A wrap 10 including four panels 12 and a pocket 20 is illustrated in FIG. 2. The four panels 12 are coupled together by the fasteners 14 to form the wrap 10. The hook-type fasteners 14 are secured to the outer surface of adjoining panels 12. The pocket 20 is secured to the interior of the wrap 10 by the hook-type fasteners 26.

Multiple pockets 20 can be secured to the interior surface of a wrap 10, formed of multiple panels 12. Accordingly, the wearer can use multiple pockets to apply thermo packs, weights or support, to multiple surfaces of a body part. For example, in a wrap worn around a wearer's knee, two pockets can be used to simultaneously apply thermo packs to both sides of the knee.

Figure 5:
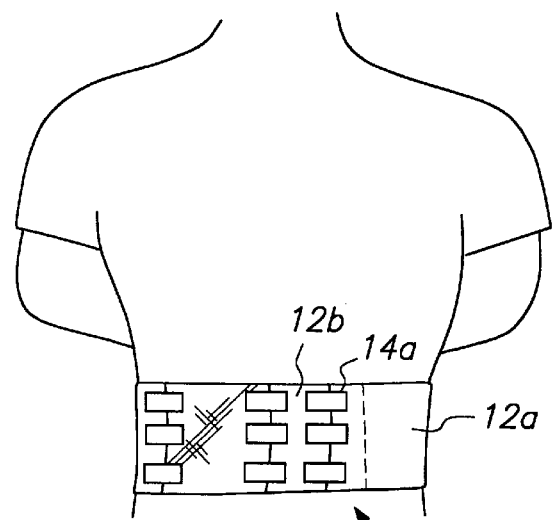
FIG. 5 illustrates the placement of a wrap, including multiple panels, around the lower back of a wearer.
Figure 6:
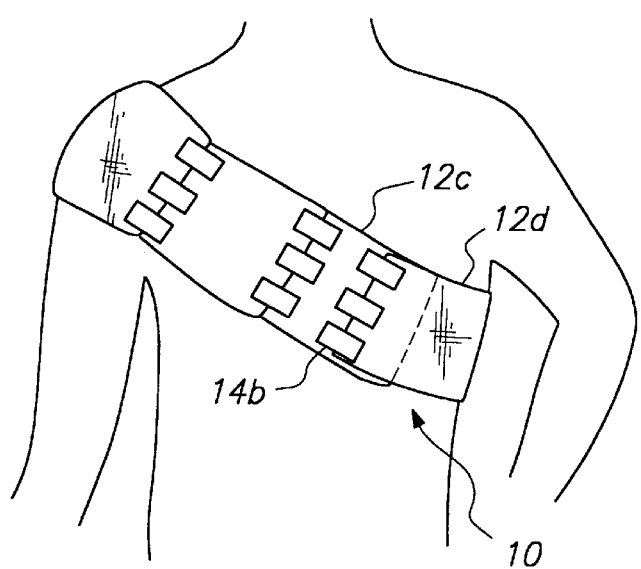
FIG. 6 illustrates the placement of a wrap, including multiple panels, around the shoulder and chest of a wearer.
Figure 7:
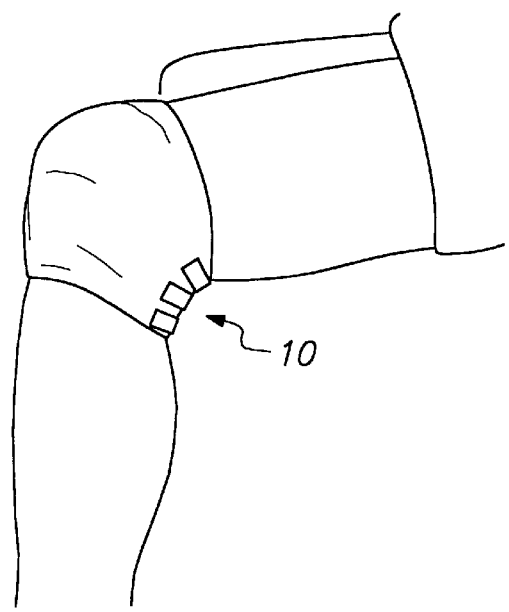
FIG. 7 illustrates the placement of a wrap, according to the present invention, around the knee of a wearer.

FIGS. 5–7 illustrate wraps, according to the present invention, of various sizes positioned over different body parts. FIG. 5 illustrates a wrap 10, including multiple panels, positioned around a wearer's lower back. In order to snugly and securely fit around the wearer's back, the panel 12a is overlapped and secured to the middle of the panel 12b by the fasteners 14a. In this manner, the wrap 10 is snugly secured to the wearer's back without the use of straps or elastic bands. As taught above, one or more pockets 20 can be secured to the interior of the wrap 10 and applied to the wearer's lower back, side or stomach with the wrap 10 worn as illustrated in FIG. 5.

FIG. 6 illustrates a wrap 10, including multiple panels, positioned around a wearer's shoulder. In order to snugly and securely fit around the wearer's shoulder, the panel 12d is overlapped and secured to the middle of the panel 12c by the fasteners 14b. In this manner, the wrap 10 is snugly secured to the wearer's shoulder without the use of straps or elastic bands. As taught above, one or more pockets 20 can be secured to the interior of the wrap 10 and applied to the wearer's shoulder, side or chest with the wrap 10 worn as illustrated in FIG. 6.

FIG. 7 illustrates a wrap 10, including multiple panels, positioned around a wearer's knee. As taught above, one or more pockets 20 can be secured to the interior of the wrap 10 and applied to the wearer's knee with the wrap 10 worn as illustrated in FIG. 7.

The fasteners 14 are preferably sewn to the right edge of each panel 12, as illustrated in FIG. 1. It should be apparent to those skilled in the art, that the fasteners can alternatively be sewn to any or all edges of the panels in order to provide wraps in multiple configurations for treatment of different sized body areas. For example, the fasteners 14 can be attached to both the right edge and the top edge of a panel 12 for forming a wrap, having a height dimension of more than one panel 12. Alternatively, the fasteners 14 can be loose and attached to adjoining panels on any edge, by causing the hook-type surface of the fastener 14 to be secured to the loop-type surface of the panel.

Hook and loop type fasteners have been described and are preferably used to secure adjoining panels together to form a wrap. However, it should also be apparent to those skilled in the art that other types of fastening means may be used to secure adjoining panels together to form a wrap. While the panels 12 are preferably rectangular in shape, it should also be obvious that the panels 12 can be of any appropriate shape, including but not limited to square, oval or triangular.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

I claim:

1. An expandable wrap for securely fitting around a body area comprising:

a. a plurality of substantially identical panels, each panel having an exterior surface and an interior surface, wherein substantially an entire interior surface comprises a loop type fastener;

b. a hook type fastener coupled to the exterior surface of each panel for coupling to the interior surface of an adjoining panel, thereby securing the panels together, wherein the fasteners can be coupled to any portion of the surfaces of the panels for forming a body encircling loop of any length; and c. a pocket having a pocket-mounted hook type fastener configured for attaching to the interior surface of each of the panels such that the same interior surface is configured for use for attachment to the hook type fastener coupled to the exterior surface of each panel and also to the pocket-mounted hook type fastener.

2. The expandable wrap as claimed in claim 1 wherein the exterior and interior surfaces of each panel are both made of a fabric loop-type material.

3. The expandable wrap as claimed in claim 2 wherein the panel further comprises a middle layer of rubber insulating foam material.

4. The expandable wrap as claimed in claim 1 wherein the fasteners are hook-type fasteners.

5. The expandable wrap as claimed in claim 4 wherein the fasteners are sewn to the exterior surface of the panels.

6. The expandable wrap as claimed in claim 4 wherein the fasteners are for coupling to the exterior surface of the panels.

7. The expandable wrap as claimed in claim 1 wherein the pocket is removably attached to any portion of the interior surface of the panels by a hook-type fastener.

8. The expandable wrap as claimed in claim 1 wherein the pocket holds thermo packs.

9. The expandable wrap as claimed in claim 1 wherein the pocket holds a weight.

10. The expandable wrap as claimed in claim 1 wherein the pocket holds a support.

11. The expandable wrap according to claim 1 wherein the panels are substantially similar in size.

12. An expandable wrap for securely fitting around a body area and applying a elective one of a hot thermo pack, a cold thermo pack, a weight and a support to the body area, comprising:

a. a plurality of substantially identical panels, each panel having an exterior surface and an interior surface, further wherein substantially the entire interior surface comprises a loop type fastener;

b. a hook type fastener coupled to the exterior surface of each panel for securing the panels together, wherein the hook fasteners can be coupled to any portion of the interior surfaces of the panels for forming a body wrap of any length; and c. a pocket including a pocket fastener for removably attaching the pocket to any portion of the interior surface of a panel and holding a selective one of the hot thermo pack, the cold thermo pack, a weight and a support such that the same interior surface is configured for use for attachment to the hook type fastener coupled to the exterior surface of each panel and also to the pocket fastener.

13. The expandable wrap as claimed in claim 12 wherein the exterior and interior surfaces of each panel are both covered by a same fabric loop-type material.

14. The expandable wrap as claimed in claim 13 wherein the panel fasteners are hook-type fasteners for securely fitting to the exterior surface of the panels.

15. The expandable wrap as claimed in claim 14 wherein the pocket fastener is a hook-type fastener for securely fitting to the interior surface of a panel.

\* \* \* \* \*